United States Patent
Xu et al.

(10) Patent No.: US 10,737,120 B2
(45) Date of Patent: Aug. 11, 2020

(54) DETECTING CONSISTENCY BETWEEN RADIATION FIELD AND LIGHT FIELD

(71) Applicant: Shanghai Neusoft Medical Technology Co., Ltd., Shanghai (CN)

(72) Inventors: Han Xu, Shenyang (CN); Zhichao Jiang, Shenyang (CN); Lin Zhang, Shenyang (CN); Ming Li, Shenyang (CN)

(73) Assignee: Shanghai Neusoft Medical Technology Co., Ltd., Shanghai (CN)

( * ) Notice: Subject to any disclaimer, the term of this patent is extended or adjusted under 35 U.S.C. 154(b) by 0 days.

(21) Appl. No.: 16/154,737

(22) Filed: Oct. 9, 2018

(65) Prior Publication Data
US 2019/0105515 A1    Apr. 11, 2019

(30) Foreign Application Priority Data
Oct. 9, 2017   (CN) .......................... 2017 1 0930472

(51) Int. Cl.
*A61N 5/10*   (2006.01)
(52) U.S. Cl.
CPC ......... *A61N 5/1075* (2013.01); *A61N 5/1049* (2013.01); *A61N 2005/1054* (2013.01);
(Continued)
(58) Field of Classification Search
CPC ................ A61N 5/1075; A61N 5/1049; A61N 2005/1076
See application file for complete search history.

(56) References Cited

U.S. PATENT DOCUMENTS

| | | | |
|---|---|---|---|
| 7,056,019 B1 * | 6/2006 | Hanson | A61B 6/583 378/18 |
| 2002/0181660 A1 * | 12/2002 | Reinstein | A61N 5/1048 378/205 |

(Continued)

FOREIGN PATENT DOCUMENTS

| CN | 202622812 U | 12/2012 |
|---|---|---|
| CN | 104754226 A | 7/2015 |

(Continued)

OTHER PUBLICATIONS

Njeh et al. ("A simple quality assurance test tool for the visual verification of light and radiation field congruent using electronic portal images device and computed radiography", Njeh et al. Radiation Oncology 2012, 7:49, http://www.ro-journal.com/content/7/1/49) (Year: 2012).*

(Continued)

*Primary Examiner* — Hugh Maupin
(74) *Attorney, Agent, or Firm* — Kilpatrick Townsend & Stockton, LLP

(57) ABSTRACT

Methods and devices for detecting consistency between an invisible radiation field and a visible light field are provided. In an example, the method includes: an invisible radiation field is obtained by controlling a size of an opening of a beam limiting device; a first projection image is captured by an Electron Portal Imaging Device (EPID) as a distribution map of the invisible radiation field; a visible light field is obtained by turning on a light field lamp without changing the size of the opening of the beam limiting device; a phantom is positioned at each of vertices of the visible light field; a second projection image is captured by the EPID as a vertex distribution map of the visible light field; and deviation information between the invisible radiation field and the visible light field is determined according to the (Continued)

distribution map of the invisible radiation field and the vertex distribution map of the visible light field.

17 Claims, 4 Drawing Sheets

(52) U.S. Cl.
CPC ............... *A61N 2005/1056* (2013.01); *A61N 2005/1076* (2013.01)

(56) References Cited

U.S. PATENT DOCUMENTS

| | | |
|---|---|---|
| 2014/0247354 A1 | 9/2014 | Knudsen et al. |
| 2016/0023019 A1* | 1/2016 | Filiberti ............... A61N 5/1077 600/1 |

FOREIGN PATENT DOCUMENTS

| | | |
|---|---|---|
| CN | 105983182 A | 10/2016 |
| JP | 2016221156 A | 12/2016 |

OTHER PUBLICATIONS

CN First Office Action dated Jun. 3, 2019 in the corresponding CN application (application No. 201710930472.0).

* cited by examiner

DETECTING CONSISTENCY BETWEEN RADIATION FIELD AND LIGHT FIELD

CROSS REFERENCE TO RELATED APPLICATIONS

This application claims priority to Chinese Patent Application No. 2017109304720 and filed on Oct. 9, 2017, the entire content of which is incorporated herein by reference.

BACKGROUND

In the medical radiotherapy technology, before radiotherapy is performed on a subject or when radiotherapy is being performed on the subject, tumors and normal organs are monitored in real time by medical imaging equipment. In this way, the radiation of the high-energy ray beam can be adjusted in real time according to changes in the tumor position, so that the radiation field of the high-energy ray beam follows the target volume tightly, so as to ensure that the tumor position is accurately irradiated.

Since high-energy rays are invisible to the naked eye, if the tumor position is accurately radiated by the high-energy ray beam, a visible light field of a visible light beam can assist in high-energy ray localization. In this case, if the light field of the visible light beam and the radiation field of the high-energy ray beam are highly coincident, the accuracy of the radiation field of the high-energy ray beam is relatively high.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

DETAILED DESCRIPTION

Figure 1:
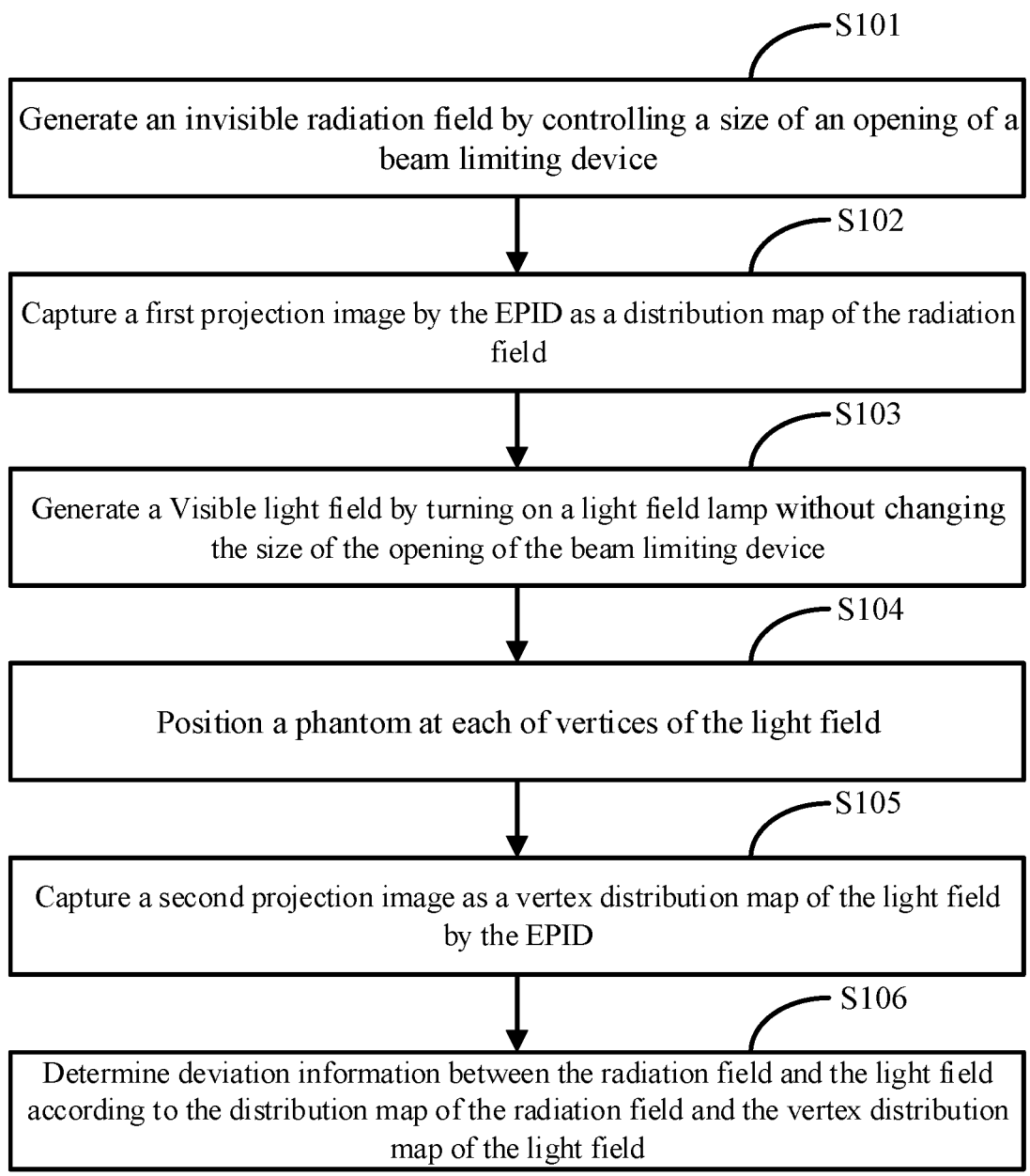
FIG. 1 is a flowchart of a method of detecting consistency between an invisible radiation field and a visible light field according to one or more examples of the present disclosure.

The technical solutions in examples of the present disclosure are clearly and completely described in the following with reference to the drawings in the examples of the present disclosure. It is obvious that the described examples are only a part of the examples of the present disclosure, and not all of the examples. All other examples obtained by a person skilled in the art based on the examples of the present disclosure without inventive efforts belong to the scope of the present disclosure.

An invisible radiation field refers to a projection area of a high-energy ray beam (such as, X-ray beam, γ-ray beam and so on) emitted by a ray generating device (such as, linear particle accelerator) in an imaging plane. A visible light field refers to an area defined by a visible light beam emitted by a visible light field lamp mounted on the ray generating device in the imaging plane. It is noted that the imaging plane refers to a plane which is through an isocenter of the ray generating device and perpendicular to a central ray of the high-energy ray beam. In addition, the light field lamp may be installed inside a treatment head of the ray generating device, so as to make a path of the visible light beam emitted by the light field lamp and a path of the high-energy ray beam consistent as much as possible. In this way, the position of the radiation field can be determined by the light field. In the present disclosure, the light field lamp is provided to simulate a ray source of the ray generating device, and the path of the visible light beam emitted by the light field lamp is as consistent as possible with the path of the high-energy ray beam.

During the irradiation on a tumor position of a subject with the high-energy ray beam emitted by the ray generating device, the light field and the radiation field keeps coincident. In this way, the detection efficiency in clinical treatment can be improved by reducing the time for determining the position of each of components in the ray generating device; the accuracy of the high-energy ray irradiation position can be ensured by completely irradiating the lesion position; and the undesired irradiation on the non-lension position can be avoided. The overall exposure dose to the subject is reduced and at some cases, complication is avoided.

The present disclosure provides a method of detecting consistency between an invisible radiation field and a visible light field. In the method, an EPID (Electron Portal Imaging Device) is used to capture projection images to respectively obtain a distribution map of the radiation field and a vertex distribution map of the light field. Deviation information between the light field and the radiation field is determined by comparing the distribution map of the radiation field and the vertex distribution map of the light field. The method of detecting consistency between the radiation field and the light field provided by the disclosure does not limit a size of an invisible radiation field and can be performed freely.

FIG. 1 is a flowchart of a process of a method of detecting consistency between an invisible radiation field and a visible light field according to one or more examples of the present disclosure. The process includes:

At step S101, an invisible radiation field is obtained by controlling a size of an opening of a beam limiting device.

The method of detecting consistency between the radiation field and the light field provided by examples of the disclosure can be applied to the ray generating device, such as linear particle accelerator. The ray generating device includes the beam limiting device. The high-energy ray beam emitted by the ray generating device passes through the opening of the beam limiting device and is then projected on the imaging plane. Therefore, the size of the opening of the beam limiting device may affect a size of the radiation field.

In an example, the size of the opening of the beam limiting device can be arbitrarily adjusted. The size of the opening of the beam limiting device is firstly determined. The high-energy-ray beam emitted by the ray generating device then passes through the opening of the beam limiting device and is projected on the imaging plane, so as to obtain the radiation field.

At step S102, a first projection image is captured by the EPID as a distribution map of the radiation field.

Figure 7:
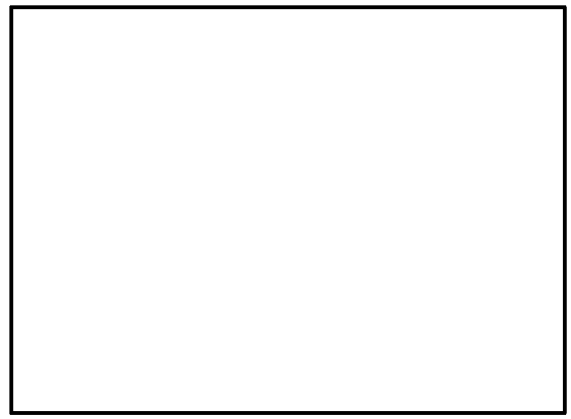
FIG. 7 is a schematic diagram of a distribution map of the invisible radiation field according to one or more examples of the present disclosure.

In practical applications, the ray generating device is provided with the EPID. In an example, the EPID is provided directly below the ray generating device for capturing projection images which is projected on the imaging plane. The first projection image is taken as the distribution map of the radiation field. As shown in FIG. 7, it is a distribution map of the radiation field according to an example. In the example, since the shape of the opening of the beam limiting device is a rectangle, the shape of the distribution map of the radiation field is also rectangular.

At step S103, a visible light field is obtained by turning on a visible light field lamp without changing the size of the opening of the beam limiting device.

In an example, to maintain consistent projection standards, the size of the opening of the beam limiting device is kept unchanged. The light field lamp mounted on the ray generating device is turned on. The visible light beam emitted by the light field lamp passes through the opening of the beam limiting device and is projected onto the imaging plane to obtain the light field. The light field refers to an area which is defined by the visible light beam in the imaging plane.

At step S104, a phantom is positioned at each of vertices of the light field.

Figure 2:
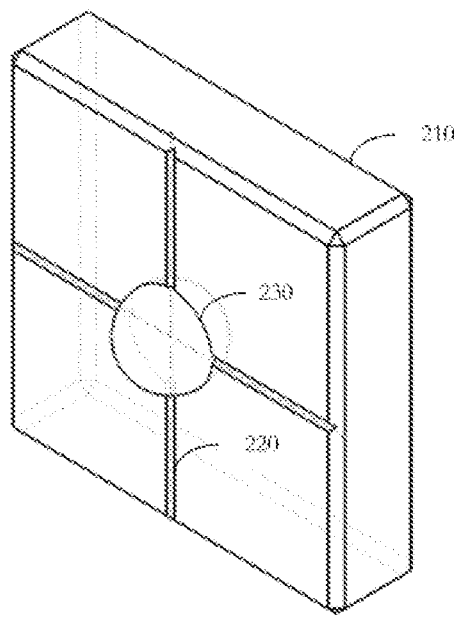
FIG. 2 is a schematic diagram of a phantom for detecting consistency between an invisible radiation field and a visible light field according to one or more examples of the present disclosure.

Examples of the present disclosure further provide a phantom for detecting consistency between an invisible radiation field and a visible light field. Referring to FIG. 2, which is a schematic diagram of a phantom for detecting consistency between an invisible radiation field and a visible light field according to one or more examples of the present disclosure. Each of the phantoms includes a base 210 and two cross engraved lines 220 which are perpendicular with each other and disposed on a surface of the base 210. A point of intersection between the two cross engraved lines 220 is provided with a marker 230, and attenuation of a high-energy ray beam by the base 210 is less than attenuation of the high-energy ray beam by the marker 230. It is noted that the shape of the phantom shown in FIG. 2 is substantially a rectangular prism, and may be other shapes, which is not limited in the present disclosure.

The base 210 may be made of a low attenuation material, such as, resin material, such as, acrylic. The marker 230 embedded in the point of intersection between the two cross engraved lines 220 may include a metal sphere, such as steel sphere, lead sphere, copper sphere and so on; and also include other shapes, such as a cube, which is not limited in the present disclosure.

Figure 3:
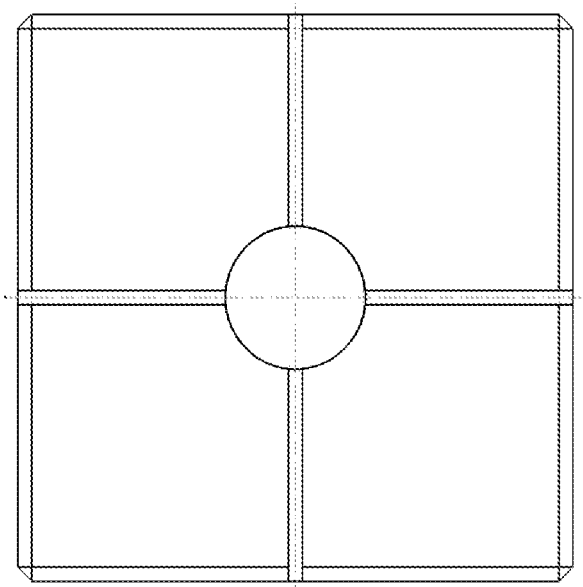
FIG. 3 is a top view of the phantom for detecting consistency between an invisible radiation field and a visible light field according to one or more examples of the present disclosure.
Figure 4:
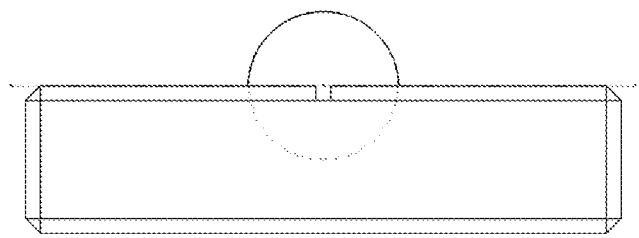
FIG. 4 is a front view of the phantom for detecting consistency between an invisible radiation field and a visible light field according to one or more examples of the present disclosure.

To facilitate the understanding of the structure of the phantom for detecting consistency between an invisible radiation field and a visible light field provided by examples of the present disclosure, a top view and a front view of the phantom for detecting consistency between an invisible radiation field and a visible light field are further provided, as shown in FIGS. 3-4.

Figure 5:
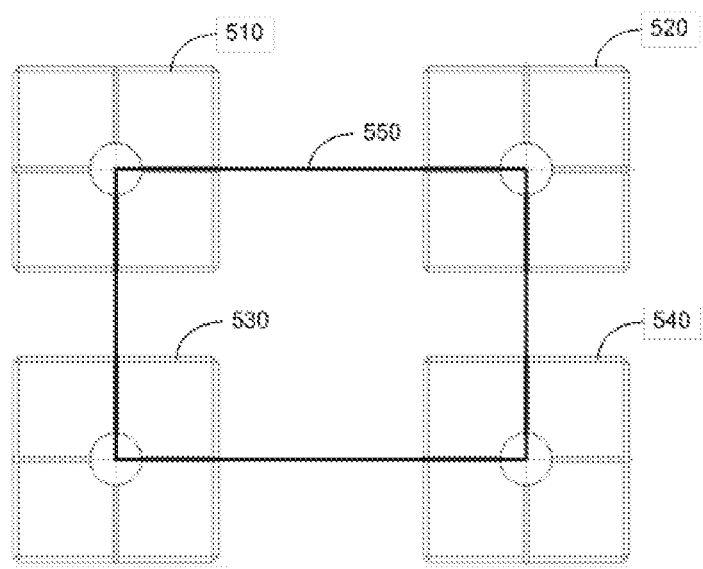
FIG. 5 is a schematic diagram of a process for determining vertex positions of a visible light field with the phantom according to one or more examples of the present disclosure.

In an example, positioning the phantom at the vertex of the light field includes: adjusting the two cross engraved lines of the phantom to coincide with two sides defining the vertex of the light field respectively. In this way, the center of the marker of each of the phantoms is aligned with the corresponding vertex of the light field. FIG. 5 is a schematic diagram of a process for determining vertex positions of the light field with the phantoms according to one or more examples of the present disclosure. As shown in FIG. 5, phantom 510, phantom 520, phantom 530 and phantom 540 are respectively placed at the respective vertices of the light field 550.

At step S105, a second projection image as a vertex distribution map of the light field is captured by the EPID, where the vertex distribution map includes a projection of respective vertices of the light field.

Figure 6:
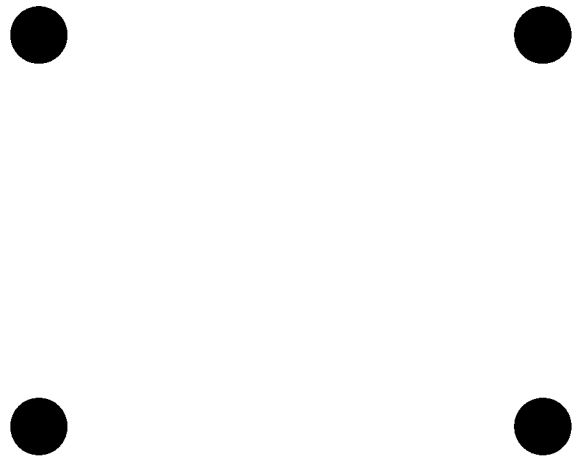
FIG. 6 is a schematic diagram of a vertex distribution map of a visible light field according to one or more examples of the present disclosure.

The phantoms are respectively placed at the corresponding vertex of the light field as shown in the step S104. In an example, the position of each of the phantoms is kept unchanged, and in this case, the second projection image as the vertex distribution map of the light field is captured by the EPID. The vertex distribution map includes the projection of respective vertices of the light field. FIG. 6 is a vertex distribution map according to an example. As shown in FIG. 6, the vertex distribution map includes the projection of each of the four vertices of the light field.

In addition, to ensure that the projection of each of the vertices of the light field is completely displayed in the vertex distribution map, in an example, before capturing the second projection image by the EPID as the vertex distribution map of the light field, the size of the opening of the beam limiting device is enlarged until each of the phantoms is within or entirely within the light field. In this way, the second projection image captured by the EPID includes the projection of respective vertices of the light field which is determined by the phantoms.

At step S106, deviation information between the radiation field and the light field is determined according to the distribution map of the radiation field and the vertex distribution map of the light field.

In an example, if the deviation information is greater than a preset threshold, it is determined that the light field and the radiation field are inconsistent; if the deviation information is less than or equal to the preset threshold, it indicates that the light field and the radiation field are consistent.

In an example, the deviation information between the light field and the radiation field includes a distance between two sides of each side pair. For example, firstly, sides of the light field are determined according to the projection of the respective vertices in the vertex distribution map of the light field. Hereinafter, the sides of the light field are takes as second sides. Secondly, side pairs are determined according to first sides of the radiation field and the second sides of the light field. Thirdly, the distance between two sides of each side pair is calculated, where the deviation information includes the distance between two sides of each side pair. It is noted that each side pair includes one of the first sides of the radiation field and one of the second sides of the light field. Theoretically, the one of the first sides of the radiation field coincides with the one of the second sides of the light field. In a case where the shape of the radiation field is a rectangle, it is assumed that four sides of the radiation field are respectively indicated by S11, S12, S13 and S14; and four sides of the light field are respectively indicated by S21, S22, S23 and S24. Four side pairs are then determined. A first pair of the four side pairs includes S11 and S21. A second pair of the four side pairs includes S12 and S22. A third pair of the four side pairs includes S13 and S23. A fourth pair of the four side pairs includes S14 and S24. The distance between two sides of each side pair is calculated. If the distance between two sides of any side pair is greater than the preset threshold, it is determined that the light field and the radiation field are inconsistent.

Since both of the distribution map of the radiation field and the vertex distribution map of the light field are in a coordinate system of the imaging plane, in this coordinate system, the coordinate of each of vertices of the radiation field (hereinafter may also be referred to as each of first vertices of the radiation field) and the coordinate of each of vertices of the light field (hereinafter may also be referred to as each of second vertices of the light field) can be obtained. Based on this, determining the side pairs according to the first sides of the radiation field and the second sides of the light field includes: generating a first linear equation for each of the first sides based on the distribution map of the radiation field; generating a second linear equation for each of the second sides based on the projection of the respective second vertices in the vertex distribution map of the light field; and determining the side pairs respectively including one of the first sides and one of the second sides, where a slope difference between the first linear equation for the first side in the side pair and the second linear equation for the second side in the side pair is less than or equal to a first threshold, and an intercept difference between the first linear equation for the first side in the side pair and the second linear equation for the second side in the side pair is less than or equal to a second threshold.

In an example, it is assumed that the first linear equation for one of the first sides is represented by the following formula (1):

$$a_1 x + b_1 y + c_1 = 0 \qquad (1).$$

The second linear equation for one of the second sides is represented by the following formula (2):

$$a_2 x + b_2 y + c_2 = 0 \qquad (2).$$

If the absolute of the slope difference between the slope $$-\frac{a_1}{b_1}$$

of the formula (1) and the slope $$-\frac{a_2}{b_2}$$

of the formula (2) is less than or equal to the first preset threshold, and the absolute of the intercept difference between the intercept $$-\frac{c_1}{b_1}$$

of the formula (1) and the intercept $$-\frac{c_2}{b_2}$$

of the formula (2) is less than or equal to the second preset threshold, the one of the first sides and the one of the second sides are determined as the side pair. Similarly, each of the side pairs can be determined. By calculating the distance between two sides of each side pair, the deviation information between the radiation field and the light field can be obtained. In an example, the distance between two sides of the side pair including the one of the first sides and the one of the second sides is obtained with the following formula (3):

$$d = \frac{\left| \frac{c_1}{b_1} - \frac{c_2}{b_2} \right|}{\sqrt{1 + \frac{\left( \frac{a_1}{b_1} + \frac{a_2}{b_2} \right)^2}{4}}} \times d_{pixel}. \qquad (3)$$

Where, $d_{pixel}$ represents a length of a single pixel.

In an example, when the marker is a sphere and the shape of the radiation field is the rectangle, a process for determining second sides of the light field according to the projection of the respective vertices in the vertex distribution map of the light field includes: firstly, determining a coordinate of each of the second vertices of the light field by an algorithm of detecting a center of a circle based on Hough transform; secondly, arbitrarily selecting coordinates of two second vertices and determining a linear equation based on the coordinates of the two second vertices; and thirdly, obtaining two values by introducing coordinates of the other two second vertices into the linear equation. If the two values are both positive (>0) or negative (<0), it indicates that the linear equation corresponds to one of the second sides of the light field.

In another example, the deviation information between the light field and the radiation field includes a distance between two vertices of each vertex pair. For example, firstly, each of first vertex coordinates of the radiation field is determined based on the distribution map of the radiation field; secondly, vertex pairs are determined according to the projection of the respective vertices in the vertex distribution map of the light field and each of the first vertex coordinates; and thirdly, a distance between two vertices of each of the vertex pairs is calculated.

Since both of the distribution map of the radiation field and the vertex distribution map of the light field are in the coordinate system of the imaging plane, each of the vertex pairs is determined according to the projection of the respective vertices in the vertex distribution map of the light field and each of the first vertex coordinates. For example, firstly, each of second vertex coordinates of the light field is determined based on the projection of the respective vertices in the vertex distribution map of the light field; secondly, for each of the second vertex coordinates, one of the first vertex coordinates which is closest to the second vertex coordinate is found; and thirdly, the vertex pair is determined according to the second vertex coordinate and the one of the first vertex coordinates which is closest with the second vertex coordinate. That is, the vertex pair includes the the second vertex coordinate and the one of the first vertex coordinates closest to the second vertex coordinate.

In the method of detecting consistency between the radiation field and the light field provided by the present disclosure. The EPID is used to capture projection images to respectively obtain the distribution map of the radiation field and the vertex distribution map of the light field. Deviation information between the light field and the radiation field is determined by comparing the distribution map of the radiation field and the vertex distribution map of the light field. The method of detecting consistency between the radiation field and the light field provided by the disclosure does not limit a size of an invisible radiation field and can be performed freely. That is, by the method, consistency between the radiation field and the light field can be detected freely, thereby improving the flexibility of detecting consistency between the radiation field and the light field.

Figure 8:
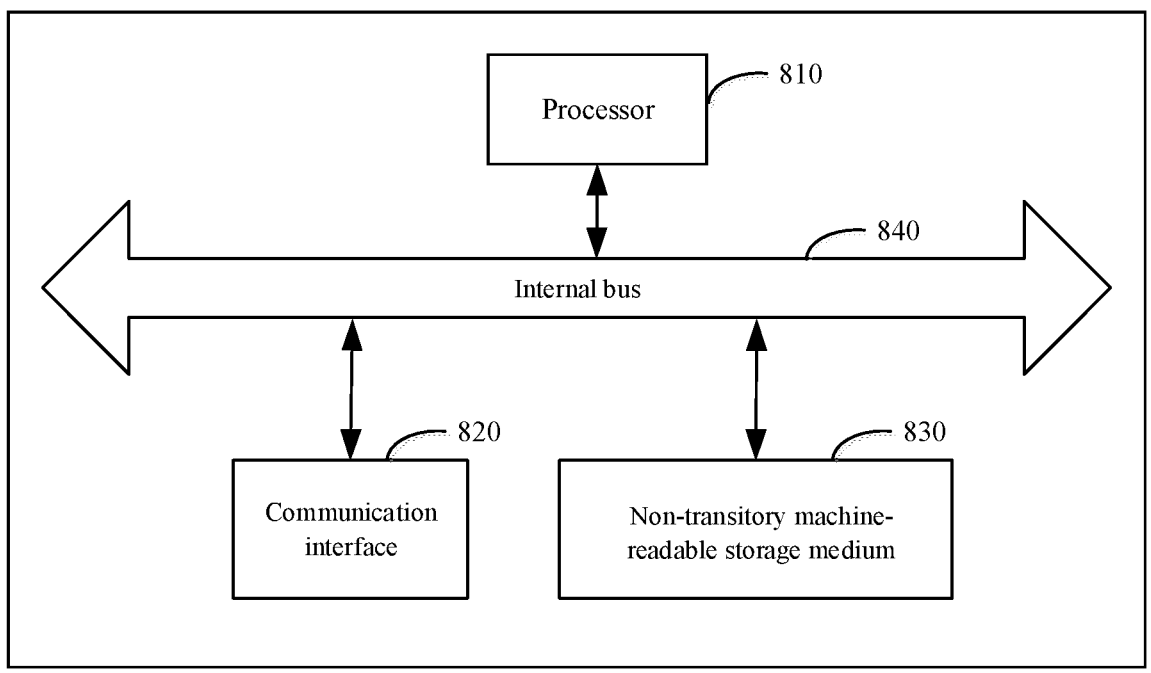
FIG. 8 is a hardware structural diagram of a device for detecting consistency between an invisible radiation field and a visible light field according to one or more examples of the present disclosure.

Corresponding to the above-mentioned method of detecting consistency between the radiation field and the light field, a device for detecting consistency between the radiation field and the light field is further provided. FIG. 8 is a hardware structural diagram of a device for detecting consistency between an invisible radiation field and a visible light field according to an example. Referring to FIG. 8, the device includes a processor 810, a communication interface 820, an non-transitory machine readable storage medium 830 and a bus 840. The processor 810, the communication interface 820, and the non-volatile machine readable storage medium 830 communicate with each other via the bus 840. The device for detecting consistency between the radiation field and the light field can include other hardware according to actual needs, and the present disclosure does not limit this.

In an example, by invoking machine executable instructions stored in the non-transitory machine readable storage medium 830, the processor 810 is caused to perform the method of detecting consistency between the radiation field and the light field. Details may refer to the above method of detecting consistency between the radiation field and the light field, which are omitted for brevity.

In an example, a non-transitory machine-readable storage medium is also provided. The non-transitory machine-readable storage medium stores machine executable instructions which are executed by one or more processors. The machine executable instructions are executed by the processor to perform the method of detecting consistency between the radiation field and the light field. Details may refer to the above method of detecting consistency between the radiation field and the light field, which are omitted for brevity.

For the device example, since it basically corresponds to the method example, it can be referred to the description of the method example. The device example described above is merely illustrative, wherein the units described as separate components may or may not be physically separated, and the components displayed as units may or may not be physical units, they may be located a place, or distributed to multiple network units. Some or all of the modules may be selected according to actual needs to implement the purpose of the technical solution of the present disclosure. Those of ordinary skill in the art can understand and implement without any creative effort.

It should be appreciated that although different information may be described using the terms such as first, second, third, etc. in the present disclosure, such information should not be limited to these terms. Such terms are used only to distinguish the same type of information from each other. For example, without departing from the scope of the present disclosure, the first information may also be referred to as the second information and similarly, the second information may also be referred to as the first information. Depending on the context, the word "if" as used herein may be interpreted as "when" or "as" or "in response to determining".

The above description is merely preferred examples of the present disclosure and is not intended to limit the present disclosure in any form. Although the present disclosure is disclosed by the above examples, the examples are not intended to limit the present disclosure. Those skilled in the art, without departing from the scope of the technical scheme of the present disclosure, may make a plurality of changes and modifications of the technical scheme of the present disclosure by the method and technical content disclosed above.

Therefore, without departing from the scope of the technical scheme of the present disclosure, based on technical essences of the present disclosure, any simple alterations, equal changes and modifications should fall within the protection scope of the technical scheme of the present disclosure. Accordingly, other examples are within the scope of the following claims.

What is claimed is:

1. A method of detecting consistency between an invisible radiation field and a visible light field, comprising:
   generating an invisible radiation field by controlling a size of an opening of a beam limiting device;
   capturing a first projection image with an Electron Portal Imaging Device (EPID) as a distribution map of the invisible radiation field;
   generating a visible light field by turning on a light field lamp without changing the size of the opening of the beam limiting device;
   positioning a phantom at each of vertices of the visible light field, wherein the phantom comprises:
   a base,
   two cross engraved lines which are perpendicular with each other and disposed on a surface of the base,
   a marker positioned at a point of intersection between the two cross engraved lines,
   wherein attenuation of an X-ray beam by the base is less than attenuation of the X-ray beam by the marker;
   capturing a second projection image by the EPID to generate a vertex distribution map of the visible light field, wherein the vertex distribution map comprises a projection of respective vertices of the visible light field; and
   determining deviation information between the invisible radiation field and the visible light field based on the distribution map of the invisible radiation field and the vertex distribution map of the visible light field.

2. The method of claim 1, wherein the base comprises acrylic.

3. The method of claim 1, wherein:
   the marker comprises a metal sphere; and
   a center of the marker is located substantially at the point of intersection between the two cross engraved lines.

4. The method of claim 1, wherein capturing the second projection image by the EPID comprises:

enlarging the size of the opening of the beam limiting device such that each of the phantoms is within the visible light field; and capturing the second projection image by the EPID.

5. The method of claim 1, wherein positioning the phantom at the vertex of the visible light field comprising:

adjusting the two cross engraved lines of the phantom to substantially coincide with two sides of the visible light field intersecting at the vertex.

6. The method of claim 1, wherein determining the deviation information between the invisible radiation field and the visible light field according to the distribution map of the invisible radiation field and the vertex distribution map of the visible light field comprises:

determining sides of the visible light field according to the projection of the respective vertices in the vertex distribution map of the visible light field, wherein the sides of the visible light field are taken as second sides;

determining side pairs according to first sides of the invisible radiation field and the second sides of the visible light field;

calculating a distance between two sides of each of the side pairs, wherein the deviation information comprises the distance between the two sides of the side pair.

7. The method of claim 6, wherein determining the side pairs according to the first sides of the invisible radiation field and the second sides of the visible light field comprises:

generating a first linear equation for each of the first sides based on the distribution map of the invisible radiation field; and generating a second linear equation for each of the second sides based on the projection of the respective vertices in the vertex distribution map of the visible light field, wherein each of the side pairs comprises one of the first sides and one of the second sides, wherein a slope difference between the first linear equation for the first side in the side pair and the second linear equation for the second side in the side pair is less than or equal to a first threshold, and wherein an intercept difference between the first linear equation for the first side in the side pair and the second linear equation for the second side in the side pair is less than or equal to a second threshold.

8. The method of claim 1, wherein determining the deviation information between the invisible radiation field and the visible light field according to the distribution map of the invisible radiation field and the vertex distribution map of the light field comprises:

determining each of first vertex coordinates of the invisible radiation field based on the distribution map of the invisible radiation field;

determining vertex pairs according to the projection of the respective vertices in the vertex distribution map of the visible light field and each of the first vertex coordinates; and calculating a distance between two vertices of each of the vertex pairs, wherein the deviation information comprises the distance between two vertices of each of the vertex pairs.

9. The method of claim 8, wherein determining vertex pairs according to the projection of the respective vertices in the vertex distribution map of the visible light field and each of the first vertex coordinates comprises:

determining each of second vertex coordinates of the visible light field based on the projection of the respective vertices in the vertex distribution map of the visible light field;

for each of the second vertex coordinates, finding one of the first vertex coordinates which is closest to the second vertex coordinate; and determining a vertex pair which comprises the second vertex coordinate and the one of the first vertex coordinates closest to the second vertex coordinate.

10. A device for detecting consistency between an invisible radiation field and a visible light field, comprising:

a processor; and a non-transitory machine readable storage medium storing instructions, which, when executed cause the processor to perform a method, comprising:

generating an invisible radiation field by controlling a size of an opening of a beam limiting device;

capturing a first projection image with an Electron Portal Imaging Device (EPID) as a distribution map of the invisible radiation field;

generating a visible light field by turning on a light field lamp without changing the size of the opening of the beam limiting device;

positioning a phantom at each of vertices of the visible light field, wherein the phantom comprises:

a base, two cross engraved lines which are perpendicular with each other and disposed on a surface of the base, a marker positioned at a point of intersection between the two cross engraved lines, wherein attenuation of an X-ray beam by the base is less than attenuation of the X-ray beam by the marker;

capturing a second projection image by the EPID to generate a vertex distribution map of the visible light field, wherein the vertex distribution map comprises a projection of respective vertices of the visible light field; and determining deviation information between the invisible radiation field and the visible light field based on the distribution map of the invisible radiation field and the vertex distribution map of the visible light field.

11. The device of claim 10, wherein the base comprises acrylic.

12. The device of claim 10, wherein:

the marker comprises a metal sphere; and a center of the marker is located substantially at the point of intersection between the two cross engraved lines.

13. The device of claim 10, wherein when capturing the second projection image by the EPID, the processor is caused by the machine executable instructions to:

enlarge the size of the opening of the beam limiting device such that each of the phantoms is within the visible light field; and capture the second projection image by the EPID.

14. The device of claim 10, wherein when determining the deviation information between the invisible radiation field and the visible light field according to the distribution map of the invisible radiation field and the vertex distribution map of the visible light field, the processor is caused by the machine executable instructions to:

determine sides of the visible light field according to the projection of the respective vertices in the vertex distribution map of the visible light field, wherein the sides of the visible light field are taken as second sides;

determine side pairs according to first sides of the invisible radiation field and the second sides of the visible light field;

calculate a distance between two sides of each of the side pairs, wherein the deviation information comprises the distance between the two sides of the side pair.

15. The device of claim 14, wherein when determining the side pairs according to the first sides of the invisible radiation field and the second sides of the visible light field, the processor is caused by the machine executable instructions to:

generate a first linear equation for each of the first sides based on the distribution map of the invisible radiation field;

generate a second linear equation for each of the second sides based on the projection of the respective vertices in the vertex distribution map of the visible light field; and wherein each of the side pairs comprises one of the first sides and one of the second sides, wherein a slope difference between the first linear equation for the first side in the side pair and the second linear equation for the second side in the side pair is less than or equal to a first threshold, and wherein an intercept difference between the first linear equation for the first side in the side pair and the second linear equation for the second side in the side pair is less than or equal to a second threshold.

16. The device of claim 10, wherein when determining the deviation information between the invisible radiation field and the visible light field according to the distribution map of the invisible radiation field and the vertex distribution map of the visible light field, the processor is caused by the machine executable instructions to:

determine each of first vertex coordinates of the invisible radiation field based on the distribution map of the invisible radiation field;

determine vertex pairs according to the projection of the respective vertices in the vertex distribution map of the visible light field and each of the first vertex coordinates; and calculate a distance between two vertices of each of the vertex pairs, wherein the deviation information comprises the distance between two vertices of each of the vertex pairs.

17. The device of claim 16, wherein when determining vertex pairs according to the projection of the respective vertices in the vertex distribution map of the visible light field and each of the first vertex coordinates, the processor is caused by the machine executable instructions to:

determine each of second vertex coordinates of the visible light field based on the projection of the respective vertices in the vertex distribution map of the visible light field;

for each of the second vertex coordinates, find one of the first vertex coordinates which is closest to the second vertex coordinate; and determine a vertex pair which comprises the second vertex coordinate and the one of the first vertex coordinates closest to the second vertex coordinate.

* * * * *